US00PP12833P2

(12) United States Plant Patent
Sherman

(10) Patent No.: US PP12,833 P2
(45) Date of Patent: Aug. 6, 2002

(54) PLUM TREE NAMED 'GULFROSE'

(75) Inventor: Wayne B. Sherman, Gainesville, FL (US)

(73) Assignees: Thomas D. Stadsklev; Florida Foundation Seed Producers, Inc., both of Greenwood, FL (US)

( * ) Notice: Subject to any disclaimer, the term of this patent is extended or adjusted under 35 U.S.C. 154(b) by 0 days.

(21) Appl. No.: 09/643,661

(22) Filed: Jul. 12, 2000

(51) Int. Cl.[7] ..... A01H 5/00
(52) U.S. Cl. ..... Plt./184
(58) Field of Search ..... Plt./184

*Primary Examiner*—Bruce R. Campell
*Assistant Examiner*—Susan B. McCormick

(57) ABSTRACT

A Japanese-type plum tree characterized by its low winter chilling, high heat requirement for adaptation to central and north Florida, mid- to late May ripening of dark red skin, blood flesh, semi-freestone fruit and regular, high annual fruit production.

1 Drawing Sheet

BACKGROUND OF THE NEW VARIETY

The present invention relates to a new and distinct variety of Japanese type plum (*Prunus salicina* Lindl.) tree which is named 'Gulfrose' and, more particularly to a plum tree which is adapted to central and north Florida winter climate with annual and heavy crops which ripen in the mid- to late May in the adapted area. Contrast is made to 'Gulfruby' (unpatented) plum for reliable description and contrast. This new variety is a promising candidate for commercial success in Florida because it bears fruit ripening in spring when few plums are available from the U.S.

ORIGIN OF THE VARIETY

This plum tree originated from the University of Florida stone fruit breeding programs at Gainesville from an open pollination of 'Gulfruby' (unpatented) plum, and hereinafter will be referred to varietally as 'Gulfrose'. The present variety was selected in 1995, and has been tested as Fla. 95-4 plum. 'Gulfrose' has been asexually propagated by budding onto 'Flordaguard' (unpatented) peach rootstock in an experimental orchard at Gainesville for 2 succeeding generations, which shows that characteristics of the tree are established and uniformly transmitted. 'Flordaguard' does not impart any known characteristics to the scion variety different than other root-knot nematode resistant peach rootstocks.

SUMMARY OF THE VARIETY

This new and distinct variety of plum tree is large, vigorous, and semi-spreading in growth. It has an estimated chilling requirement of 275 chill units, but appears to have a high heat requirement for breaking dormancy in that 'Gulfrose' trees bloom before the earliest standard Japanese varieties at Gainesville, but with or after the same standard Japanese varieties in north Florida locations. Winter temperatures of 14° F. in Florida have not damaged wood or flower and leaf buds. 'Gulfrose' is adapted to the winters of north central and north Florida, overlapping the second half of the flowering period in 'Gulfruby', 'Gulfbeauty' (U.S. Plant Pat. No. 11,224), and 'Gulfblaze' (U.S. Plant Pat. No. 10,873) plums, and 'Gulfrose' is cross pollinated with pollen from each of them. None of these plums are self fertile and all require cross pollination for fruiting. 'Gulfrose' is a regular and productive bearer of medium size, firm, semi-freestone fruit with good eating quality and a slightly tart skin. The fruit is further characterized by having deep red skin, firm, blood flesh, hanging on the tree 10 days after maturity (shipping ripe) and ripening 7 to 10 days after 'Gulfruby'. Fruit set is very high and fruit thinning may be required to prevent limb breakage and size fruit properly. The new variety is distinguished from 'Gulfruby' in having blood flesh, later ripening fruit and a higher degree of resistance in leaves, twigs, and fruit to bacterial leaf spot. Fruit of 'Gulfrose' are highly resistant to sun scald ('Gulfruby' is highly susceptible), concentric skin cracks, and split stones. Leaves have moderate resistance to leaf scald.

BRIEF DESCRIPTION OF THE DRAWING

The drawing is a color photograph, showing a typical stem, leaves, and ripe fruit as viewed from the stem, distal end, and side views perpendicular and parallel to the suture. The photograph colors are as nearly true as is reasonably possible in a color representation of this type.

DETAILED BOTANICAL DESCRIPTION

The following is a detailed description of 'Gulfrose' plum tree, its flowers, foliage, and fruit based on observations of specimens grown near Gainesville, Fla. on 'Flordaguard' peach rootstock. Color names (except those in common terms) with a capital letter designate values based upon the Pantone Book of Color published in 1990 by Harry N. Abrams, Inc. N.Y. 'Gulfrose' plum tree and its fruit as described below may vary slightly in detail due to climate, soil conditions, and cultural practices under which the variety may be grown.

Tree:

*Size.*—Moderate and in the medium range for a Japanese plum. Trees reach the desired pruning height of 2 meters by the end of their third year of growth when they have a spread of 1.5 meters.

*Vigor.*—Moderately vigorous and in the medium range for a Japanese plum.

*Form.*—Semi-spreading.

*Density.*—Moderately dense in branching habit and in the medium range for a Japanese plum.

*Shape.*—Rounded.

*Productivity.*—Productive and requires fruit thinning to prevent limb breakage and to size fruit when cross pollinated with a suitable pollinizer, a plant that provides pollen in cross pollination.

*Bearing.*—Regular and uniform on both spurs and whips.

*Cold hardiness.*—Hardy under Florida temperatures of 14° F.

*Chilling requirement.*—Estimated 275 chill units based on bloom time and fruitfulness following annually diverse winter chilling in Florida.

Trunk:

*Size.*—Medium, attaining 5 to 6 cm trunk diameter at a height of 15 cm above the soil line at the end of 3 years.

*Texture.*—Medium shaggy, developing a moderate amount of peeling bark.

*Color.*—Gray, Chinchilla (Pantone 17-1109).

Branches:

*Size.*—Terminal shoot growth of a meter is common on bearing trees, averaging 8 to 12 mm diameter at the base and 2 mm diameter at the terminals as branches have long terminal growth giving the appearance of whippy fruiting branches.

*Texture.*—Smooth on new wood with a medium amount of lenticels developing on older wood, attaining size found on trunk and old scaffolds.

*Lenticels.*—Moderate number and in the medium range for Japanese plum. Size is 1 to 2 mm long and 0.2 to 0.3 mm wide on second year old wood.

*Color.*—Light green, Leek Green (Pantone 15-0628), in current season's growth (whips) in May.

*Fruiting.*—Fruits on spurs and branches (whips).

Leaves:

*Arrangement.*—Alternate.

*Average size.*—106 mm length, (including petiole), 36 mm wide.

*Form.*—Elliptical with acuminate tip and cuneate base.

*Margin.*—Serrulate with numerous small glands as seen at 10× magnification. One gland on each tip of a saw tooth edge of the blade from base to tip. Not visible to naked eye.

*Thickness.*—Leaf thickness and coarseness is not, by touch, distinguishable from 'Gulfruby'.

*Surface.*—Upper, reticulate; Lower, medium veined.

*Texture.*—Glabrous.

*Average petiole size.*—12 mm length, 2 mm diameter, and Grass Green (Pantone 15-6437).

*Petiole glands.*—1 to 2 small globose glands on upper portion of petiole or at base of leaf blade. Color is dark brown, Marron (Pantone 18-1415) on tips and similar in color, size, and number to glands on 'Gulfruby'.

*Color.*—Deep green upper surface, Cactus (Pantone 18-0130); Gray green lower surface, Cedar (Pantone 16-0526); Main vein on lower surface is Leek Green (Pantone 15-0628).

Flower buds:

*Size.*—Slightly shorter and thicker than leaf bud at the node.

*Length.*—Medium, 2 mm length; 1 mm diameter.

*Form.*—Ovate and free.

*Color.*—Brown, Glazed Ginger (Pantone 18-1154).

Flowers:

*Blossom period.*—About 10 days, but extending to 20 days under low temperatures.

*Size, number and shape.*—Small to medium (25–27 mm diameter) flowers. The 5 petals are 11 to 12 mm length, 6 to 7 mm width, and have a smooth, wavy margin. Petal apex is obtuse and base is cuneate.

*Pedicel.*—The pedicel is 5 to 6 mm length, slightly less than 1 mm diameter, and Lettuce Green (Pantone 13-0324).

*Pollen.*—Abundant, yellow, Pastel Yellow (Pantone 11-0616), and functions well as a pollinizer, a male parent in cross-pollination.

*Color.*—White.

*Date.*—Starting February 10 to 20 at Gainesville.

*Scented.*—Strongly fragrant and pleasant.

*Anther color.*—Yellow, Daffodil (Pantone 14-0850).

*Calyx cup.*—Medium size (6 mm diameter outside, 3 mm deep inside below the petal base).

*Fertility.*—Requires cross-pollination for fruit set due to pollen self incompatibility.

Fruit:

*Maturity date.*—Yearly variable, but beginning May 15 to 25 at Gainesville, and extending 7 to 10 days from first to last harvest.

*Weight.*—60 to 70 grams.

*Size.*—Length 4.7 cm; Width 4.7 cm.

*Form.*—Round.

*Suture.*—Slightly furrowed at stem end.

*Base.*—Nearly round, slightly flat.

*Apex.*—Round.

*Cavity.*—Circular at top to bottom. 3 mm depth; 10 mm wide at top; 1 mm wide at bottom.

*Stem.*—Medium at 5 to 7 mm length, 1 to 1.5 mm diameter, and light green, Beechnut (Pantone 14-0425).

Flesh:

*Texture.*—Firm and fine.

*Fibers.*—Small and tender.

*Flavor or eating quality.*—Sweet flesh with slightly tart skin and no bitterness.

*Juice.*—Juicy.

*Aroma.*—Moderately strong.

*Color.*—Deep red, Pompeian Red (Pantone 18-1658).

*Cavity.*—None at tip end of endocarp (stone).

Skin:

*Thickness.*—Not unusually thick or thin for a Japanese plum.

*Texture.*—Not unusually coarse or smooth for a Japanese plum.

*Bloom (wax).*—Moderate and easily rubbed leaving a shiny surface.

*Color.*—Dull deep red, Barn Red (Pantone 18-1531) at maturity to Crushed Berry (Pantone 18-1418) when fruit softens.

*Taste.*—Slightly tart with no bitterness.

Stone:

*Type.*—Semi-freestone.

*Size.*—Length 21 mm. Width 15 mm.

*Form.*—Ovate, with an obtuse base and acute apex.

*Sides.*—Equal.

*Surface.*—Small pits throughout and on blade.

*Ridges.*—Blade on suture extending from base to tip.

*Color.*—Light brown, Coral Gold (Pantone 16-1337).

*Tendency to split.*—No splitting observed.

Use: Market.—Local and long distance for fresh dessert markets. Degree of firmness at harvest and firmness and flavor retained in refrigeration for 14 days at 7 C. indicates fruit should be highly acceptable for shipping.

Resistance to disease: High resistance to bacterial spot in fruit, leaves and stems incited by *Xanthomonas campestris* pv. *pruni* (Sm.) Dye and to leaf scald incited by *Xylellia fastidiosa* Wells et al.

We claim:

1. A new and distinct variety of plum tree, substantially as illustrated and described, which is moderately vigorous and large, and semi spreading in growth with a low winter chilling, high heat requirement for adaptation to central and north Florida producing annual crops of good flavor and eating quality fruit of medium size, semi-freestone fruit with full red skin and blood flesh which ripen about 7 to 10 days after 'Gulfruby' and having firm flesh with good shipping characteristics for its intended fresh market use.

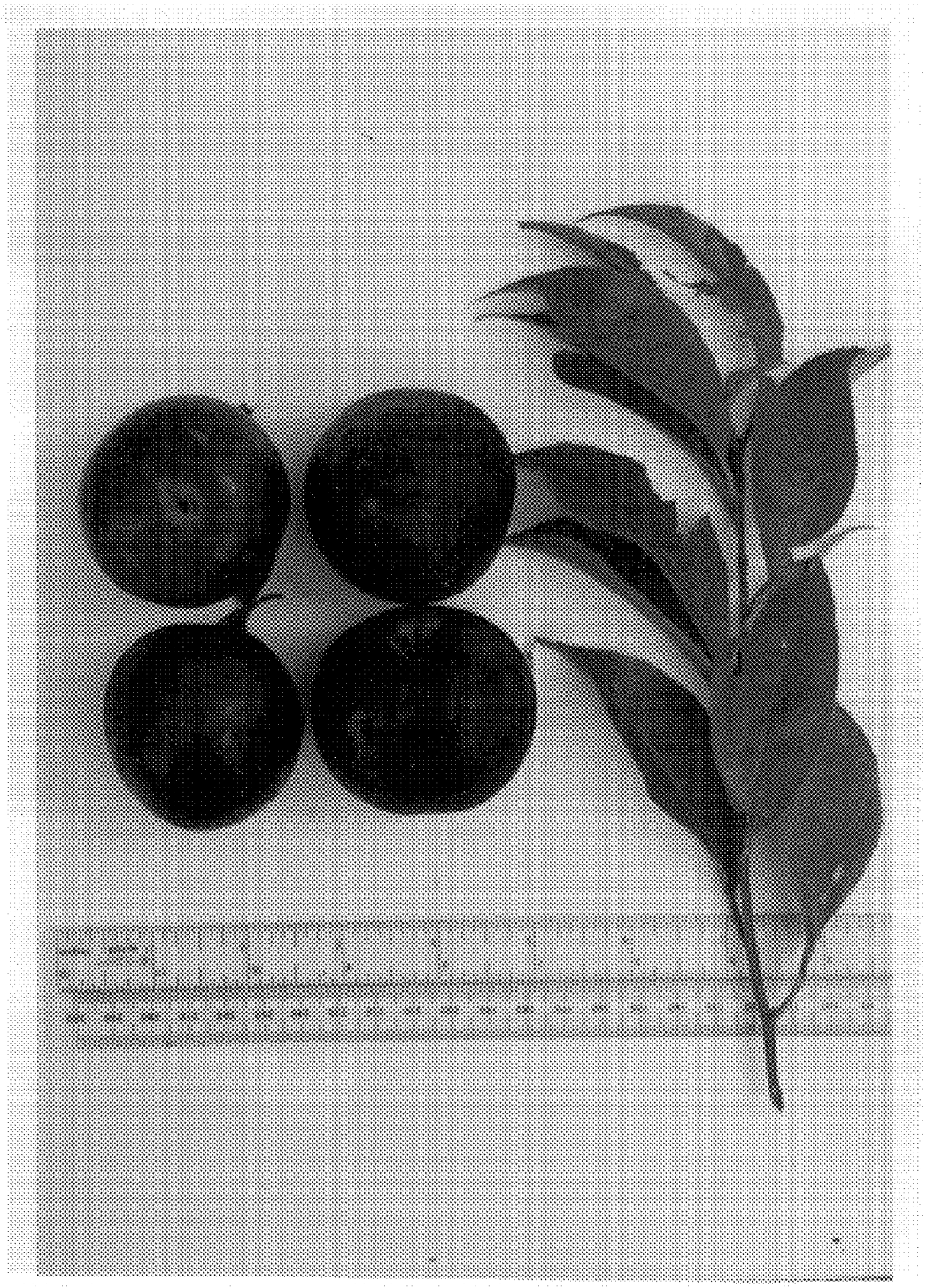

* * * * *